(12) United States Patent
Reed et al.

(10) Patent No.: US 9,352,108 B1
(45) Date of Patent: May 31, 2016

(54) RESPIRATORY MEDICAMENT NEBULIZER SYSTEM

(71) Applicants: George Ashford Reed, West Linn, OR (US); Jeffrey John Quinn, Carmel, IN (US); Brad Hayden Quinn, Indianapolis, IN (US); Patrick Finn Boileau, Newberg, OR (US)

(72) Inventors: George Ashford Reed, West Linn, OR (US); Jeffrey John Quinn, Carmel, IN (US); Brad Hayden Quinn, Indianapolis, IN (US); Patrick Finn Boileau, Newberg, OR (US)

( * ) Notice: Subject to any disclaimer, the term of this patent is extended or adjusted under 35 U.S.C. 154(b) by 0 days.

(21) Appl. No.: 14/884,599

(22) Filed: Oct. 15, 2015

(51) Int. Cl.
*A61M 11/00* (2006.01)
*A61M 15/00* (2006.01)
*A61M 16/00* (2006.01)

(52) U.S. Cl.
CPC ....... *A61M 15/0091* (2013.01); *A61M 15/0085* (2013.01); *A61M 2016/0018* (2013.01); *A61M 2205/3331* (2013.01); *A61M 2205/3592* (2013.01); *A61M 2205/8262* (2013.01)

(58) Field of Classification Search
CPC ............ A61M 11/001; A61M 11/003; A61M 11/005; A61M 11/15; A61M 11/0091; A61M 11/0085; B05B 17/06; B05B 17/0615; B05B 17/0638; B05B 17/0646; B05B 17/0661; B05B 17/0669
See application file for complete search history.

(56) References Cited

U.S. PATENT DOCUMENTS

| | | | |
|---|---|---|---|
| 7,322,349 B2 | 1/2008 | Power | |
| 2009/0242660 A1* | 10/2009 | Yu | A61M 15/0085 239/102.2 |
| 2012/0285446 A1* | 11/2012 | Van Der Mark | A61M 11/005 128/200.14 |
| 2013/0079732 A1* | 3/2013 | Burt | B05B 7/0012 604/290 |

* cited by examiner

*Primary Examiner* — Justine Yu
*Assistant Examiner* — Kathrynn Lyddane
(74) *Attorney, Agent, or Firm* — Swanson & Bratschun, L.L.C.

(57) ABSTRACT

A nebulizer system includes a body having a fluid chamber and an aerosol chamber, and a vibrator assembly positioned at an interface between the fluid chamber and the aerosol chamber. The vibrator assembly may include a diaphragm, having a fluid side and an aerosol side, defining a plurality of perforations between the fluid side and the aerosol side, and one or more vibrator elements operatively associated with the diaphragm to vibrate the diaphragm to produce aerosolized medicament projected into the aerosol chamber from the plurality of perforations. Each perforation of the plurality of perforations projects the aerosolized medicament along a respective projection path substantially normal to a plane defined by the aerosol side of the perforation, the one or more vibrator elements further being configured to angularly displace the aerosol side of the diaphragm to sweep the direction of at least one projection path.

29 Claims, 11 Drawing Sheets

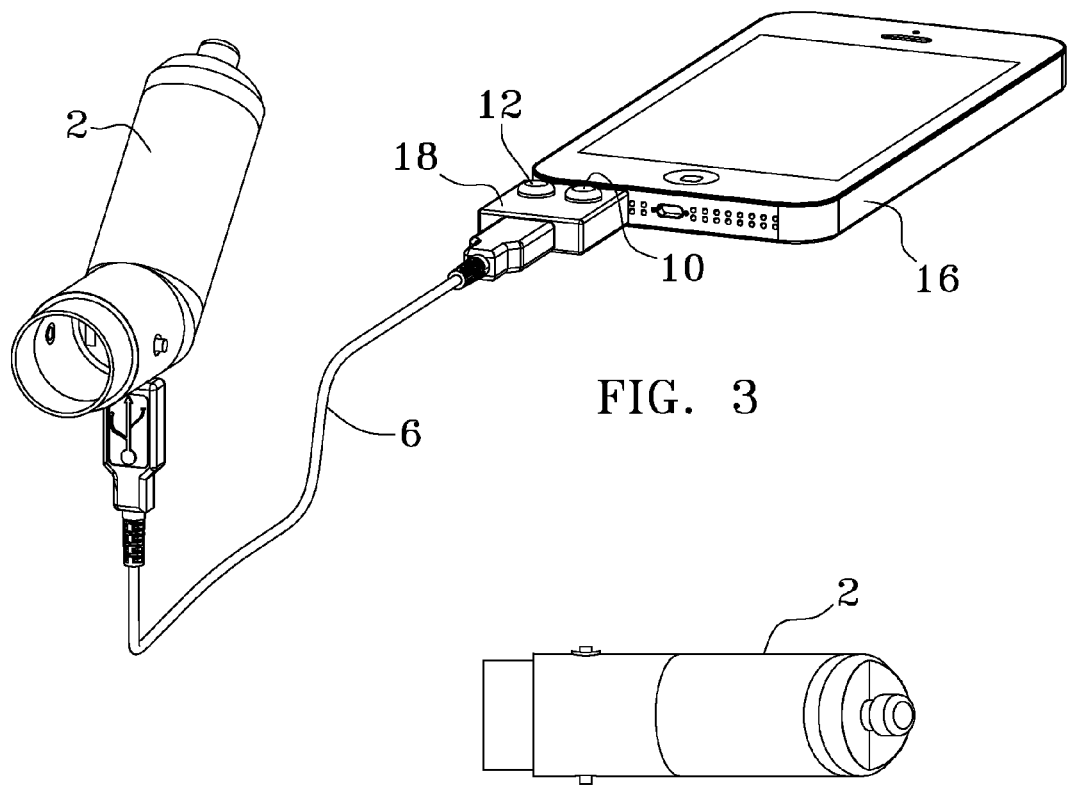
FIG. 3
FIG. 4
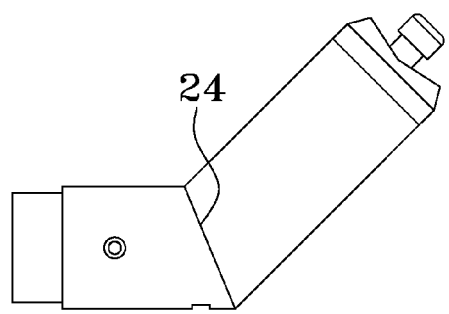
FIG. 5

FIG. 10
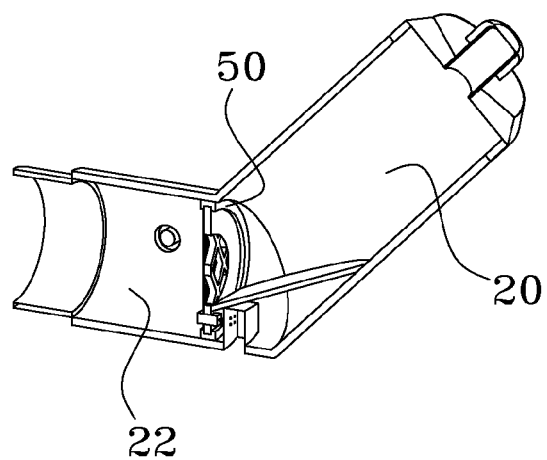
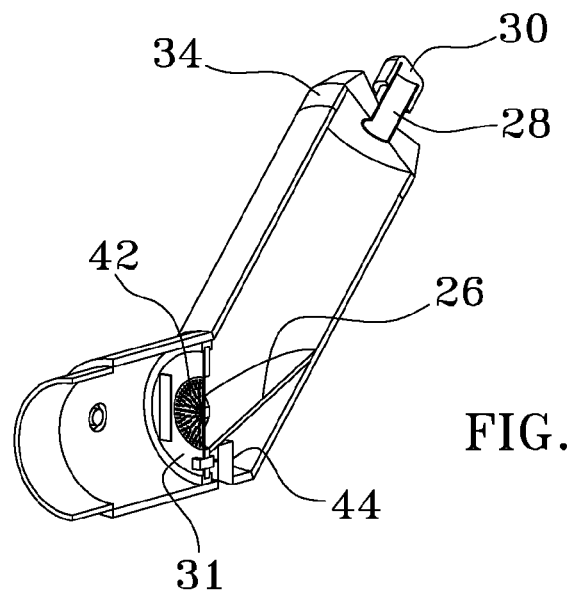
FIG. 11

RESPIRATORY MEDICAMENT NEBULIZER SYSTEM

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to medical nebulizers, and more particularly to electrical nebulizer technology.

BACKGROUND

In medicine, a nebulizer (also spelled nebuliser) is a drug delivery device used to administer a liquid medicament, or mixture of liquid medicaments, for example, bronchodilators or corticosteroids, in aerosolized form, to be inhaled into the lungs. Nebulizers are commonly used for the treatment of respiratory diseases such as cystic fibrosis, asthma and chronic obstructive pulmonary disease (COPD). In such applications, the aerosolized medicament is administered to increase a patient's lung capacity and ease labored breathing.

Many conventional electrical nebulizers utilize vibrating mesh technology wherein a liquid medicament is continuously supplied to one side of a high speed vibrating mesh element residing in a tubular housing. The rapid vibration forces the liquid medicament, through the vibrating mesh element and into the tubular housing, forming small droplets of liquid medicament, thereby generating aerosolized medicament. These nebulizers, once turned on, continuously run, generating aerosolized medicament within the housing, regardless of whether medicament is needed. These devices do not account for the amount of medicament used or track any of the parameters associated with its administration. Further, while the mesh may be sized to generate aerosol particles at a desired diameter of approximately 1 to 4.5 $\mu m$ (microns), larger particles may be generated, which travel slower than smaller particles generated behind them such that rear collisions may occur, resulting in even larger particles and increasing the mass median aerodynamic diameter (MMAD) of the aerosolized medicament delivered.

Thus, a more controllable and consistent nebulizer solution is provided by the embodiments set forth below.

BRIEF SUMMARY

In accordance with various embodiments, a system, apparatus, and method for a respiratory medicament aerosol generator with optional "breath actuated" (on-demand) operation are provided.

In one aspect, a nebulizer system with a vibrational diaphragm design, configured to sweep a projection path of aerosolized medicament, is provided. In various embodiments, the sweeping movement of the vibrator assembly may maintain the size of the aerosolized medicament droplets until the aerosolized medicament is delivered to the patient, with minimal losses of aerosol particles, thereby promoting a MMAD in the optimal 1-4.5 micron range with a low geometric standard deviation (GSD).

In another aspect, a generator nebulizer system is provided, capable of tracking, storing, and reporting nebulizer data recorded from the various sessions of medicament delivery with respect to such parameters as delivery date, time, duration, total delivered dose and the like.

In yet another aspect, a nebulizer system is provided capable of calculating and reporting the actual dose of medication delivered into a patient's lungs following a treatment.

In yet another aspect, a nebulizer system may be controlled and powered via various communications interfaces through which external devices may be connected.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIG. 3 is a front perspective view of the nebulizer utilizing a connected mobile device;

FIG. 4 is a top perspective view of the nebulizer body, in accordance with various embodiments;

FIG. 5 is a side elevation view of the nebulizer body, in accordance with various embodiments;

FIG. 10 is a side perspective cross sectional view of the nebulizer, in accordance with various embodiments;

FIG. 11 is a rear perspective cross sectional view of the nebulizer, in accordance with various embodiments;

DETAILED DESCRIPTION OF CERTAIN EMBODIMENTS

Figure 1:
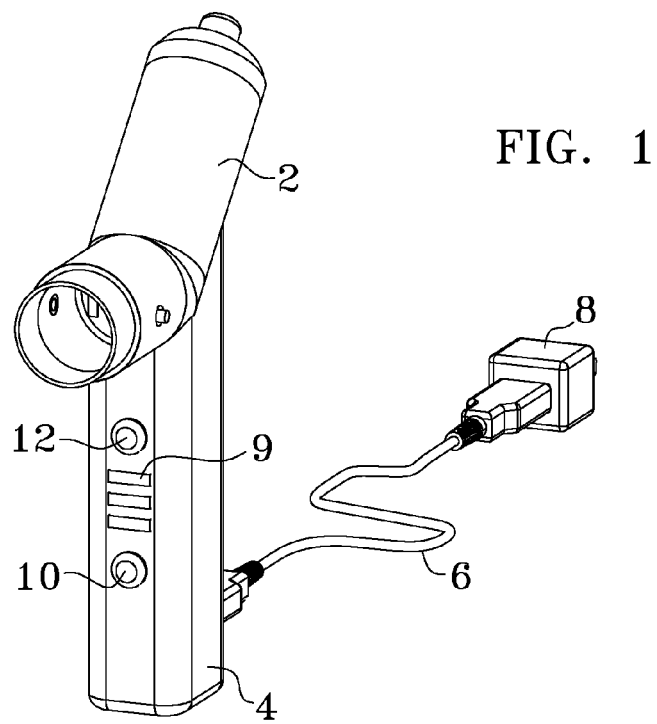
FIG. 1 is a front perspective view of an embodiment of a nebulizer utilizing a hand held support with a wall powered connection.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The present invention relates to a novel design for an improved respiratory medicament aerosol delivery device. It enables a new level of efficiency in medicament delivery at the same time as minimizing losses inherent in the prior art nebulizers. It is adapted to matingly connect with standardized respiratory devices commonly utilized in both hospital and personal respiratory therapies.

As used herein, the term "MMAD" refers to the mass median aerodynamic diameter of the aerosol particles in the holding chamber. Results may be established using an Andersen Cascade Impactor (ACI) averaging repeated readings over specified fill volumes. MMAD is generally measured in microns. The optimum or required size for aerosolized medicament particles to have a therapeutic significance is between 1 and 4.5 μm.

As used herein the term "GSD" refers to geometric standard deviation and is a dimensionless number that describes how spread out a set of numbers are, the set of numbers having a preferred average that is the same as its geometric mean. With aerosol particles, the lower the GSD the more uniform in size of the particles sampled.

As used herein, the term "inhaled dose" refers to the amount of inhaled drug for a time interval of nebulization (generally one minute).

As used herein, the term "delivered drug dose" refers to the aggregate amount of aerosol medicament determined to have reached the patient's lungs in a single nebulizer treatment/session. This may be determined when the device is operated in a breath actuation mode based on a calculation looking at, without limitation, an aerosol output per unit of time, the amount of time the vibrator assembly was oscillated/vibrated, the concentration of the drug, and any attenuation/efficiency factors taken into consideration.

As used herein, the term "diaphragm" refers to a thin, generally planar structure, which may be formed from various materials, including, without limitation, polymer, metal, and composites. The diaphragm may exhibit a series of perforations (tapered or not). The diaphragm may be used in a vibrator assembly of a nebulizer as a vibrational interface between liquid and aerosol phases of the medicament. In some embodiments, the diaphragm may include, without limitation, a vibrating mesh, perforated membrane, aperture plate, or other suitable structure.

As used herein, the term "nebulizer system" refers to a respiratory medicament aerosol generator that, via assembly with its different controllers, power supplies, adaptors and connectors can be configured to operate on, without limitation, any of: a dedicated battery power source; an external power supply; a wired power source, such as, for example, a 5 volt (V) universal serial bus (USB) based power source, or any other suitable standard, as known to those in the art; converted alternating current (AC) power from an AC outlet; or a mobile device. In various embodiments, the nebulizer system may further store, read, transmit, receive, process, and generate respiratory and nebulizer data, either through a direct cable connection, or via wireless transmission to an external computing system.

As used herein, the terms "microprocessor" or "logic chip" may refer to a computer processor on a microchip that contains all, or most of, the central processing unit (CPU) functions. The microprocessor may incorporate a real time clock and either or both of volatile/nonvolatile memory and performs arithmetic and logic operations based on input signals or data from remote devices such as a pressure transmitter, an optional condenser microphone arrangement on the vibrator assembly, or manually operated electrical switches. The processor may output operational signals that integrate with other elements of the nebulizer controller, such as the electronic control unit that turns a vibrator element on or off. It may also output algorithmically derived data to an external computing device. The external computing device may include, without limitation, a local computer, smart phone, or a health provider's network via a remote server. This data may be sent via a hard cable or through an available wireless transmitter.

In general, embodiments can employ as a processor, any device or combination of devices, that can operate to execute instructions to perform functions as described herein. Merely by way of example, and without limitation, any microprocessor can be used as a processor, including without limitation one or more complex instruction set computing (CISC) microprocessors, such as the single core and multicore processors available from Intel Corporation™ and others, such as Intel's X86 platform, including, e.g., the Pentium™, Core™, and Xeon™ lines of processors. Additionally and/or alternatively, reduced instruction set computing (RISC) microprocessors, such as the IBM Power™ line of processors, processors employing chip designs by ARM Holdings™, and others can be used in many embodiments. In further embodiments, a processor might be a microcontroller, embedded processor, embedded system, system on a chip (SoC) or the like.

As used herein, the term "processor" can mean a single processor or processor core (of any type) or a plurality of processors or processor cores (again, of any type) operating individually or in concert. The functionality described herein can be allocated among the various processors or processor cores as needed for specific implementations. Thus, it should be noted that, while various examples of processors may be described herein for illustrative purposes, these examples should not be considered limiting.

As used herein the term "USB" may refer to a plug-and-play interface, including USB 3.0 and USB Type-C, for data transfer and electrical power supply between electronic devices, such as computers, media players, keyboards, telephones, digital cameras, scanners, flash drives, joysticks and printers. Generally it supports hot swapping and eliminates the need for many adapters. The physical configuration of the connections may vary slightly and what is referred to as a USB connector may be male or female (plug or socket).

While specific embodiments may describe a USB interface for illustrative purposes, it should be noted that in some embodiments, other interfaces, protocols, connections, and connectors may be substituted, as will be appreciated by those skilled in the art. For example, other interfaces may include, without limitation, Thuderbolt, FireWire, Ethernet, and serial AT attachment (SATA) and eSATA to name but a few alternatives. Thus, these examples should not be considered limiting.

What is referred to herein as "electronic control unit" (ECU) is the hardware and software that carries out the operational instructions for a vibrator assembly, as provided by a microprocessor. The ECU may output an electrical signal that causes high frequency oscillations of the vibrator element.

Functionally, it is known that aerosols comprised of fine droplets may be generated via oscillation of a vibrational mesh. High frequency mechanical oscillations may be applied to the vibrational mesh, the vibrational mesh being a perforated membrane, in contact with a fluid, at an interface between the fluid and ambient air adjacent the fluid. The actual mechanics of this phenomenon is well described in U.S. Pat. No. 5,518,179 and Physical Principals of Ultrasonic Technology by Rozenberg, published in Plenum, the entire contents of which are incorporated herein by reference. Although the prior art discloses several different designs for perforated membranes, generally they have a series of tapered perforations formed there through with their larger opening on the side of the membrane in contact with the fluid and their smaller opening on the side ejecting the aerosol droplets (and fluid jets). The perforated membrane is generally planar, extremely thin, and lightweight. To prevent damage by the high pulse rate, the membrane may be mounted on a stiffer, planar support substrate mounted in a device at the fluid/air interface with some form of dampening to limit the vibrational movement of the support substrate within the device.

The support plate may be of sufficient mechanical rigidity to prevent flex throughout a displacement range of the perforated membrane. The support plate and perforated membrane may be caused to vibrate via one or more vibrator elements coupled to the support substrate. Vibrator elements may include, without limitation, a piezoelectric actuators, or alternatively an electrostrictive actuators. An electrical signal may be provided having a specific frequency, where the electrical signal may cause vibrations in a magnetically permeable piezoelectric material of the piezoelectric actuator. The frequency of oscillation of the piezoelectric actuator may thus be controlled as a function of the frequency of the electrical signal. In one set of embodiments, the nebulizer may utilize one or more piezoelectric ceramic transducers as vibrator elements. The design of such electrical circuits that provide the alternating electric field within the actuator is well known in the field and such a typical circuit is disclosed in U.S. Pat. No. 5,518,179.

The frequency of oscillation, size of the perforation's small opening, degree of taper, shape of the perforations, and dimensions of the perforations may be optimized to generate aerosolized medicament particles of a desired diameter. Similarly, the frequency of oscillation may be optimized, where lower oscillation frequency draws less power from the power source, and puts less stress on the membrane.

Ultrasonic nozzles provide an alternative way to produce an aerosol. Ultrasonic nozzles are a type of spray nozzle using high frequency sound waves (commonly in the range of 20-180 kHz), produced by piezoelectric transducers, acting upon a nozzle tip to create capillary waves in a liquid film until the waves reach a critical amplitude where the tip of each wave atomizes. Here, the droplet size is determined by the frequency of vibration, surface tension, and viscosity of the liquid.

Either of the above aerosol generating configurations may be utilized as part of the vibrator assembly. However, for illustrative purposes, the embodiments described herein focus on vibrator assemblies using a diaphragm, such as, without limitation, a vibrational mesh, perforated membrane, aperture plate, or other similar structures.

FIGS. 1-3 illustrate three different configurations of the nebulizer system, each of the configurations utilizing various available connectors, controllers, cables and adaptors. FIG. 1 illustrates a front perspective view of a nebulizer body 2 coupled to a hand held support 4. The hand held support 4 is further coupled to wall adapter 8 via connector cable 6. In various embodiments, the connector cable 6 may provide both power to the nebulizer, and data transmission to and from the nebulizer. In one set of embodiments, the connector cable 6 may be a USB cable, providing both charging and data transmission, connected to a 5V wall adapter 8. According to a set of embodiments, the nebulizer may require direct current (DC) input power. Thus, in some embodiments, the wall adapter 8 may be an AC to DC converter, as would be required for the charging of the DC batteries in the support 4, and operation of the nebulizer. In another set of embodiments, the nebulizer may be able to accept AC input power, the wall adapter 8 being an AC to AC converter.

In some sets of embodiments, input power and charging functionality may obtained without the wall adapter 8. For example, in various embodiments, the connector cable 6 may be a USB, Thunderbolt, SATA, eSATA, FireWire, or other cable that may be directly connected to a computer, mobile device, power strip or hub, or any other device having a compatible interface.

Figure 9:
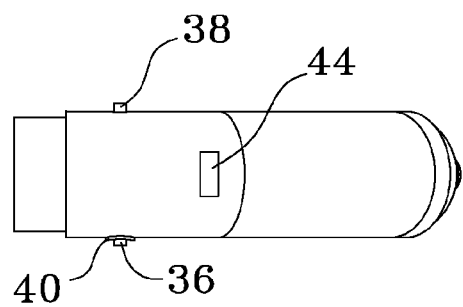
FIG. 9 is a bottom perspective view of the nebulizer body, in accordance with various embodiments.
Figure 12:
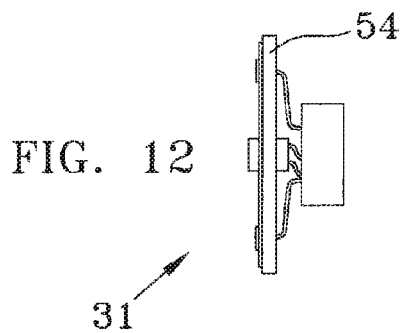
FIG. 12 is a top plan view of an embodiment of a vibrator assembly without a shock mount.
Figure 13:
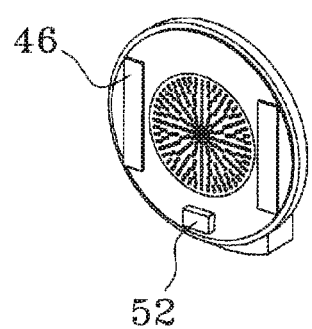
FIG. 13 is a front perspective view of the embodiment of a vibrator assembly of FIG. 12.
Figure 14:
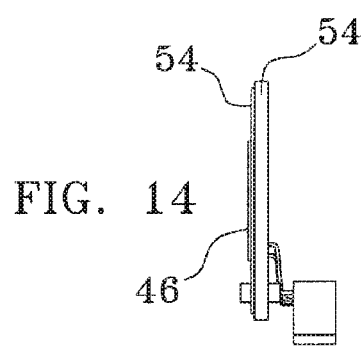
FIG. 14 is a side elevation view of the embodiment of a vibrator assembly of FIG. 12.
Figure 15:
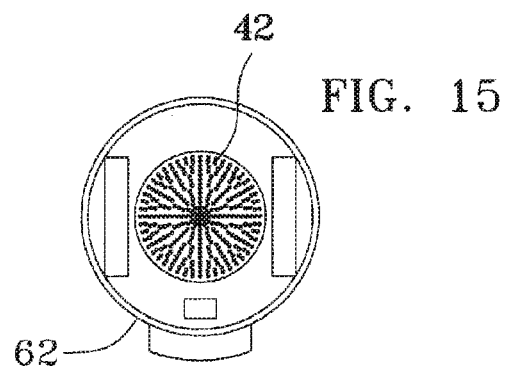
FIG. 15 is a front elevation view of the embodiment of a vibrator assembly of FIG. 12.
Figure 16:
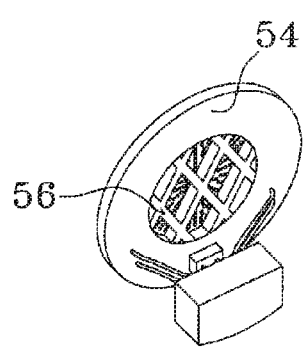
FIG. 16 is a rear perspective view of the embodiment of a vibrator assembly of FIG. 12.
Figure 17:
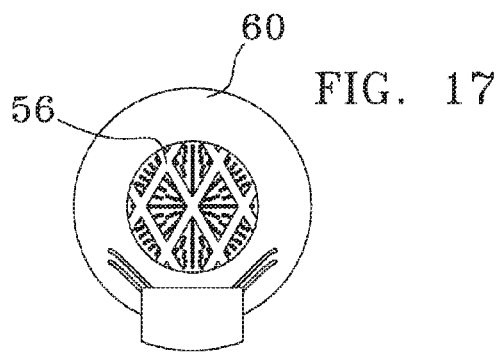
FIG. 17 is a rear elevation view of the embodiment of a vibrator assembly of FIG. 12.
Figure 18:
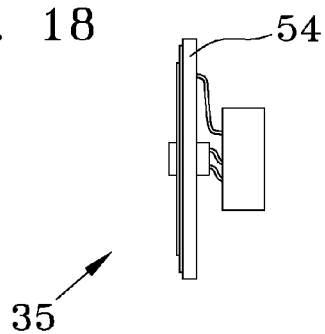
FIG. 18 is a top plan view of a first alternate embodiment of a vibrator assembly without a shock mount.
Figure 19:
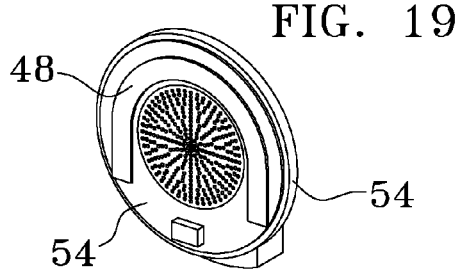
FIG. 19 is a front perspective view of the first alternate embodiment of a vibrator assembly mesh of FIG. 18.
Figure 20:
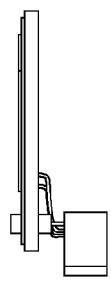
FIG. 20 is a side elevation view of the first alternate embodiment of a vibrator assembly of FIG. 18.
Figure 21:
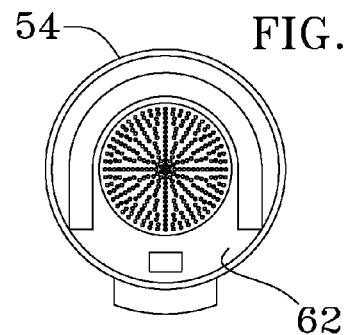
FIG. 21 is a front elevation view of the first alternate embodiment of a vibrator assembly of FIG. 18.
Figure 22:
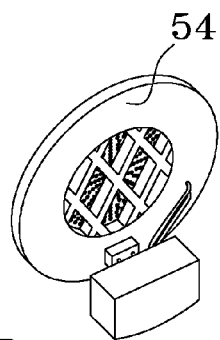
FIG. 22 is a rear perspective view of the first alternate embodiment of a vibrator assembly of FIG. 18.
Figure 23:
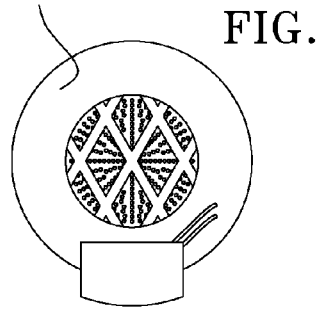
FIG. 23 is a rear elevation view of the first alternate embodiment of a vibrator assembly of FIG. 18.
Figure 24:
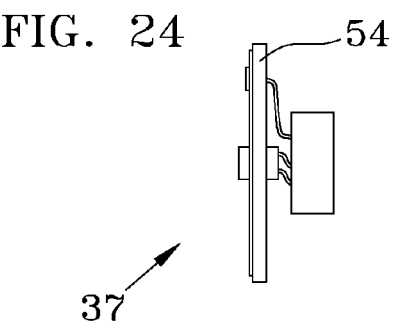
FIG. 24 is a top plan view of a second alternate embodiment of a vibrator assembly without a shock mount.
Figure 25:
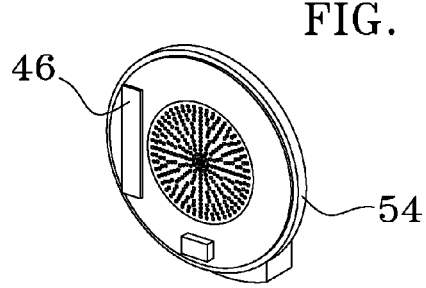
FIG. 25 is a front perspective view of the second alternate embodiment of a vibrator assembly of FIG. 24.
Figure 26:
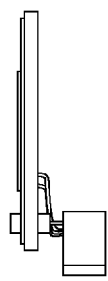
FIG. 26 is a side elevation view of the second alternate embodiment of a vibrator assembly of FIG. 24.
Figure 27:
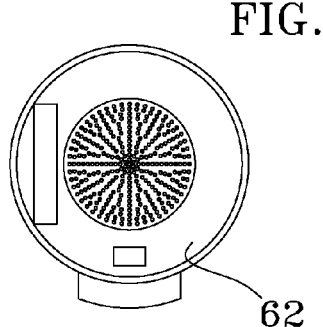
FIG. 27 is a front elevation view of the second alternate embodiment of a vibrator assembly of FIG. 24.
Figure 28:
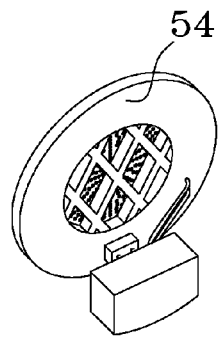
FIG. 28 is a rear perspective view of the second alternate embodiment of a vibrator assembly of FIG. 24.
Figure 29:
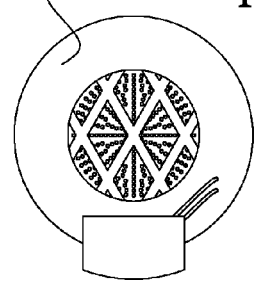
FIG. 29 is a rear elevation view of the second alternate embodiment of a vibrator assembly of FIG. 24.
Figure 30:
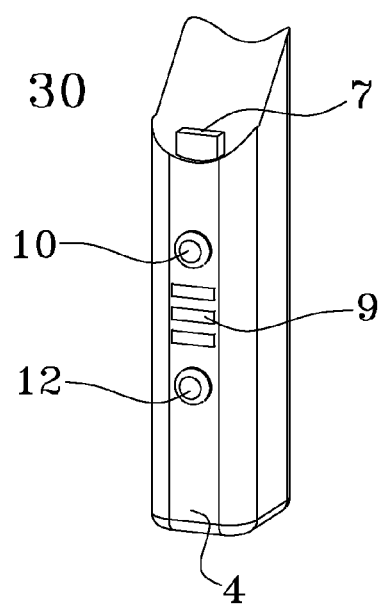
FIG. 30 is a front perspective view of the hand held support of FIG. 1.
Figure 31:
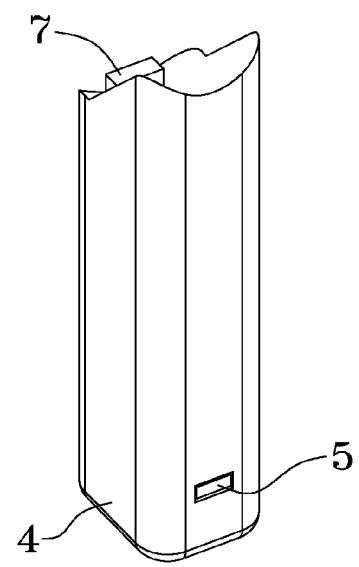
FIG. 31 is a rear perspective view of the hand held support of FIG. 1.

In various embodiments, multiple ports may be provided on the nebulizer body 2, hand held support 4, or both. In some embodiments, each of the ports may be dedicated for either power or data transfer. In some further embodiments, each of the ports may be capable of providing both power and data transfer functions. For example, with reference to FIGS. 9, 30, and 31, in various embodiments, a rear port 5 of the hand held support 4 may be provided for times when a nebulizer port 44 of nebulizer body 2 is unavailable. A male connector 7 may further be provided to couple to nebulizer port 44 for when the nebulizer body 2 is coupled to the hand held support 4, thus allowing power and data received at rear port 5 of the hand held support 4 to also reach the nebulizer body 2. In various embodiments, when a connection is made from rear port 5 to an external computer or mobile device, any data internally stored within hand held support 4 may be transferred, either automatically or manually.

The hand held support 4 may further include a power button 10, and a mode selector button 12 to switch the operation of a vibrator assembly between operation modes. According to one set of embodiments, the vibrator assembly may have at least a continuous mode, in which the vibrator elements are made to oscillate continuously while the power button 10 is in an "on" position, and a breath actuation mode where the vibrator elements may be selectively activated by the breath of a patient using the nebulizer. Mode selection may be managed by an internally housed electronic control unit of the nebulizer. In a further set of embodiments, the hand held support 4 may further include, without limitation, all of the components of an external controller 14 as described in more detail below with reference to FIG. 2, an electronic control unit, and a wireless transceiver, all in addition to the battery and battery charging electronics.

The hand held support 4 further includes a set of illumination indicators 9 placed between the buttons 10 and 12. According to one set of embodiments, the illumination indicators 9 may be used to show the status of the remaining battery power. Various embodiments further provide that the hand held support may further have an angled top surface, contoured to accept a shape of a fluid chamber 20 of the nebulizer body 2.

Figure 2:
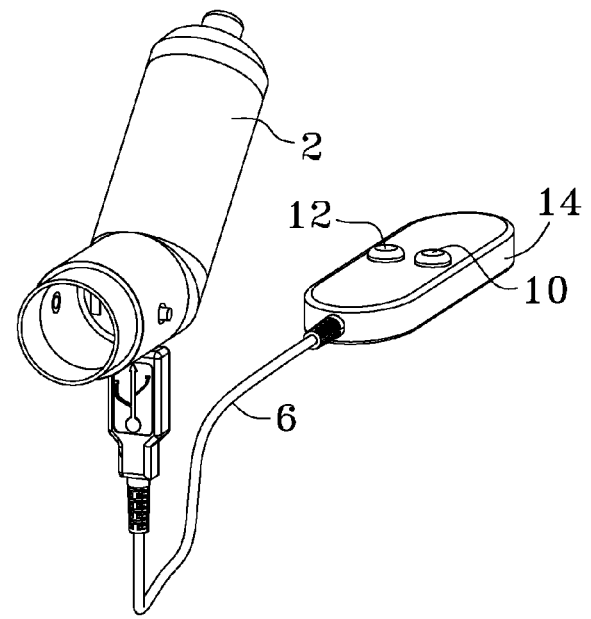
FIG. 2 is a front perspective view of an embodiment of the nebulizer utilizing an independent controller.
Figure 6:
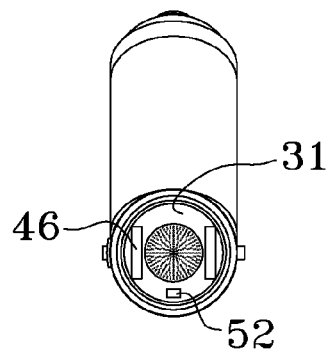
FIG. 6 is a front elevation view of the nebulizer body, in accordance with various embodiments.
Figure 7:
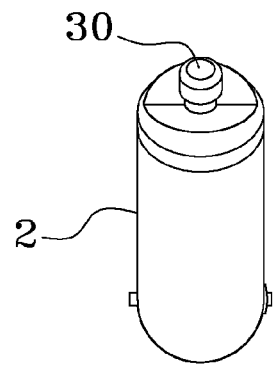
FIG. 7 is a back elevation view of the nebulizer body, in accordance with various embodiments.
Figure 8:
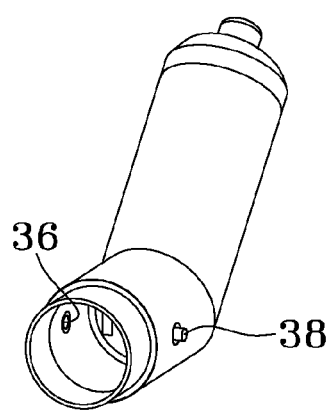
FIG. 8 is a front side perspective view of the nebulizer body, in accordance with various embodiments.

FIG. 2 shows the nebulizer body 2 coupled to the controller 14 via connector cable 6. In various embodiments, the connector cable 6 may be removable, terminating at both ends with a male connector. In other embodiments, the connector cable 6 may not be removable, at one end, joined to the controller 14, and terminate at the other end with a male connector to connect to either the nebulizer body 2, or hand held support 4. The controller 14 can be connected via connector cable 6 to a wall adapter 8, a computer, mobile device, or any other compatible interface, similar to the support 4. If such connection is made to a computer or mobile device, internally stored data of the controller 14 may be transferred. As with hand held support 4, the controller 14 may have a power button 10, as well as a mode selector button 12 to switch between operation modes of the vibrator assembly. All of the components herein may also be found in the hand held support 4.

FIG. 3 illustrates the nebulizer body 2 coupled to a mobile device (here a cell phone) 16 via a connector cable 6 that is connected to a mobile device adapter 18, that is in turn coupled to a communication port of the mobile device 16. In various embodiments, the mobile device 16 may include, without limitation, a laptop computer, tablet, smart phone, personal digital assistant, or other similar device. Furthermore, the communication port of the mobile device 16 may include, without limitation, a USB port, Thunderbolt port, a 3.5 mm port, headphone jack, eSATA port, high definition multimedia interface, and other like interfaces. Thus, in various embodiments, internally stored data from the nebulizer may be transferred to mobile device 16 over various common interfaces.

Although the connection between the nebulizer and mobile device 16, hand held support 4, and controller 14 is depicted and described in the context of a wired connection, it is to be understood that in other sets of embodiments, a wireless connection may be established between a wireless transceiver of the nebulizer and the mobile device 16, hand held support 4, or controller 14. For example, wireless connections may include, without limitation, connections over Bluetooth networks, Wi-Fi networks including wireless networks defined by 802.11 standards, cellular data networks including LTE and WiMAX, infrared connections, and the like.

In various embodiments, operational power for a microprocessor, pressure sensor, electronic control unit, and vibrator assembly of the nebulizer may be provided by the mobile device 16. Signals from the nebulizer body 2 may further be directly transmitted to the mobile device 16 which both acts as a controller and a data interpretation and presentation device. The adapter 18 may further include a power button 10, as well as a mode selector button 12 to switch between operation modes of the vibrator assembly.

As can be seen from the above illustrations and description, the respiratory medicament nebulizer system entails an interconnected array of devices that allow for the configurable operation of a nebulizer to best fit the respiratory treatment whether it be from a hospital's ventilator machine, in a health care provider's office, at the patient's home or at a location without electric power. Thus, the components of the nebulizer system may be interconnected by various types of electrical and data cable connectors 6, or wirelessly, as described above.

FIGS. 4-11 depict an embodiment of the nebulizer body 2 having a non-linear housing and a fluid chamber 20 segregated from an aerosol chamber 22. According to various embodiments, the chambers 20, 22 may each be linear tubes having their longitudinal axis angularly disposed with respect to one another. The fluid chamber 20 is adapted to hold liquid medicament and funnel it toward the fluid side of a vibrator assembly 31 regardless of the side-to-side angular positioning of the body 2. A deflection baffle 26 tapers from the interior side wall of the fluid chamber 20 to the fluid side of a vibrator assembly 31 for this reason, and to ensure the complete transfer of all medicament to the vibrator assembly 31. The deflection baffle 26 may have a curved configuration to ensure a multi directional gradient to provide a continuous feed of medicament to the vibrator assembly 31. A sealing cap 34 is provided, coupled to the top of the fluid chamber 20, the sealing cap 34 having a nipple 28 and cap 30 thereon. The cap 30 in the illustrated embodiment may be tethered around the nipple 28. The cap 30 may be of a screw on design with a set of wings extending normally from the exterior surface. This arrangement allows for the addition of fluid medicament as well as the prevention of spillage of any medicament.

The aerosol chamber 22 may further include an exhalation valve 36, and an inhalation valve 38, each of which may be one-way valves. According to one set of embodiments, the exhalation valve 36 may open externally, while inhalation valve 38 may open internally. In one set of embodiments, the exhalation valve 36 and the inhalation valve 38 may each be circumferentially opening flapper valves 40, held in place with a central post having a head larger than a central orifice in the flapper valves 40. The flapper valve 40 of the inhalation valve 38 may be located on an interior wall of the aerosol chamber 22, and the flapper valve 40 of the exhalation valve 36 may be located on an exterior wall of the aerosol chamber 22. In operation, when a patient exhales with their mouth still over the open end of the nebulizer body 2 (or a fitted mouthpiece coupled to the open end of the body) the exhalation valve 36 will open preventing unnecessary back pressurization of the diaphragm 42. The inhalation valve 38 may open upon a threshold drop in pressure below that of ambient pressure to allow for the charge of aerosolized medicament to exit the aerosol chamber 22. The threshold drop in pressure required to initiate and maintain the inhalation valve 38 open may be set higher than an initialization threshold drop in pressure required for a pressure sensor 52 to detect and send an initialization signal to the ECU, to begin oscillation of the one or more vibrator elements, when in the breath actuation mode. In some embodiments, the pressure sensor 52 may be triggered when the inspiratory effort exceeds 15 liters per minute (lpm) through the nebulizer body 2. In some alternative sets of embodiments, the exhalation and inhalation valves 36, 38 may not be located on the nebulizer body 2, but rather incorporated into a mouthpiece that may be coupled to the nebulizer body 2.

The chamber interface 24 between the fluid chamber 20 and aerosol chamber 22, defines an annular disposition between the two chambers, and operationally is where the vibrator assembly 31 is positioned within the nebulizer body 2. In various embodiments, the vibrator assembly may be kept in position by a pair of circular flanges, or other protrusions, not illustrated for visual clarity of the vibrating means, extending normally from the interior wall of the nebulizer body 2 that abut the sides of a shock mount 50. Adjacent to this interface 24, affixed in the fluid chamber 20 between the deflection baffle 26 and the outer wall of the nebulizer body 2 is a nebulizer port 44 wherein electrical leads from vibrator elements 46, 48 and the pressure sensor 52 are communicatively coupled to an ECU, and other system components. The shock mount 50, in various embodiments, may be a resilient ring positioned about a support plate 54. In other embodiments, the shock mount 50 may be a wound compression spring, disc spring, or other compressive spring mechanisms as known to those in the art.

In embodiments utilizing the hand held support 4, or the controller 14, the microprocessor and ECU may be in the same housing, along with the power button 10 and mode selector button 12. In embodiments where the nebulizer system incorporates the mobile device 16, instructions may be downloaded and written into the working memory of the mobile device 16 such that the microprocessor therein may function as the microprocessor for the nebulizer. In further embodiments, the adapter 18, connecting the nebulizer body 2 to the mobile device 16 may house the ECU, the power button 10, the mode selector button 12, any necessary power transformers and a suitable connector for mating engagement with the corresponding interface of the mobile device. In some embodiments, the connection between the adapter 18 and the mobile device 16 may be by mating engagement with model specific connectors for that mobile device 16. In many embodiments, an interface may be utilized capable of using power from the mobile device 16 to power the vibrator assembly and to use a display of the mobile device to view the nebulizer data. In various embodiments, the mobile device 16 may further be in communication over a communications network, allowing both the patient and doctor to see nebulizer data, including both the immediate results of a nebulizer treatment as well as the dose of medicament delivered to the patient.

The vibrator assembly 31 can be seen in three different configurations in FIGS. 12-29. Each vibrator assembly 31 has a fluid side 60 and an aerosol side 62. Here it can be seen that, in various embodiments, vibrator assembly 31 has a support substrate 54 with a series of orifices defining a support web 56. In one set of embodiments, the support substrate 54 may be made of stainless steel. In other embodiments, other materials may be utilized, including, without limitation, other types of metals, polymers, and composites. A diaphragm 42 may be provided, overlying the support substrate 54 on the aerosol side 62. The diaphragm 42 may have a plurality of perforations. In various embodiments, the perforations may be tapered into a cone shape, such that a smaller end of the opening is positioned to face the aerosol side. In an alternative set of embodiments, the perforations may be not be tapered, and the aerosol side of the diaphragm 42 may have a series of raised rings about each perforation. This will have a similar effect on aerosol generation. In some embodiments, the support substrate 54 may provide structural support to the diaphragm 42 to prevent folding, deformation, sliding, or other unwanted movement of the diaphragm 42. The support web 56 may further strengthen and support the diaphragm 42 to prevent vibrational damage that could occur to an unsupported diaphragm 42.

According to one set of embodiments, illustrated in FIGS. 12-17, there may be two vibrator elements 46 located on the support substrate 54 on opposite ends, but on the same face of the diaphragm 42. The vibrator elements 46 may be operated by a single ECU alternately powering the vibrator elements 46, or by a separate ECU dedicated to each of the vibrator elements 46, the actuation signal from each separate ECU being 180 degrees out of phase, as is well known in the field of piezo-electric vibrators. A shock mount 50 may be positioned around the support substrate 54, allowing for movement of the support substrate 54 within the nebulizer body 2. A pressure sensor 52, such as, without limitation, a pressure transducer, may also be mounted to the support substrate 54 of the vibrator assembly 31. The electrical leads for the vibrator elements 46, and the pressure sensor 52, may extend through or around the support substrate 54 to the nebulizer port 44.

It is to be noted that, in various embodiments, the interaction between the support substrate 54 and the diaphragm 42 enables the vibrator assembly 31 to itself act as a condenser (capacitor) microphone, able to transmit pressure fluctuations of the perforated membrane against the support web 56 as electrical potentials back to the ECU of the nebulizer. In further embodiments, the captured pressure fluctuations can be monitored over the life of the device, so as to monitor and report the condition of the diaphragm 42. This is well known technology in the field of microphones. Embodiments utilizing the vibrator assembly in this microphone-like capacity provide that the diaphragm 42 may be electrically conductive, whether throughout the membrane, or only on its outer surface as with metallic coated Mylar. Furthermore, an insulator (not illustrated) may be placed between the diaphragm 42 and the support substrate 54, each of which may have DC voltage applied to it from the ECU of the nebulizer, via two additional leads in the connector cable 6. In this manner, the diaphragm 42 may function similarly to a microphone diaphragm, and the support web 56 similarly to a back plate of a condenser microphone capsule.

FIGS. 18-23 and FIGS. 24-29 illustrate a first alternate embodiment and a second alternate embodiment of the vibrator assembly 35, 37. The first alternate embodiment of the vibrator assembly 35 utilizes a horseshoe shaped vibrator element 48. The second alternate embodiment of the vibrator assembly 37 utilizes a single vibrator element 46, positioned on one end of one face of the diaphragm 42. Thus, the vibrator assembly 37 eliminates one of the pair of vibrator elements 46 in vibrator assembly 31.

According to various embodiments, the nebulizer may be run by a power source, a ECU, and a microprocessor which may comprise all or part of the ECU. In one set of embodiments, a pressure sensor 52 may further be provided for operation of a breath actuation mode, and to measure respiratory data signals to transmit to the ECU or microprocessor. In various embodiments, the ECU may include, without limitation, at least one processor, system memory, and a set of instructions encoded on a non-transitory computer readable medium. The computer readable storage medium may include, without limitation, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH memory, any other memory chip or cartridge, a carrier wave as described hereinafter, or any other medium from which a computer can read instructions and/or code. In some sets of embodiments, the ECU may collect input signals and nebulizer data from various sensors of the nebulizer, and process the data locally at the ECU. In other sets of embodiments, the input signals and nebulizer data may be transmitted to an external system, such as a mobile device 16, hand held support 4, adapter 8, or controller 14.

In response to receiving operational signals, the ECU may turn on the vibrator assembly by actuating the vibrator elements 46, 48, such as, in one set of embodiments, a piezo ceramic transducer. According to various embodiments, the ECU, based on encoded instructions, may generate a set of nebulizer data including, without limitation, the number of nebulizer uses; the dates and times for each use; the duration of each use; the number of breaths taken per use; and the length of each of the inhalations. These values may be calculated based on input signals from the pressure sensor 52 or diaphragm 42. When the nebulizer data is received, or generated, by the ECU itself, an external computing device, hand held support 4, adapter 8, controller 14, or mobile device 16, may compile the data for a doctor's review. In some embodiments, based on input data of the type of medicament and concentration of the medicament, an actual medical dose of medicament delivered to the patient per use can be determined. In some further embodiments, the nebulizer data may also include information indicating a physical condition of the diaphragm 42, such as wear, defects, and failures in the perforated membrane.

Figure 32:
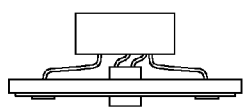
FIGS. 32 to 34 are schematic illustrations of aerosol pumping movements of the nebulizer, in accordance with various embodiments.
Figure 35:
FIGS. 35 to 37 are schematic illustrations of aerosol pumping movements of the nebulizer, in accordance with various embodiments.
Figure 33:
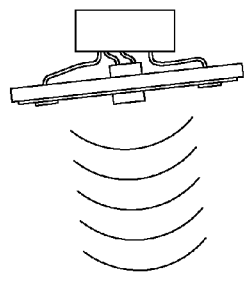
Figure 36:
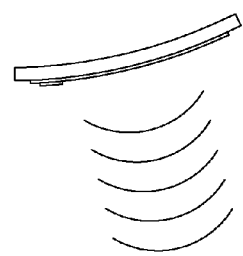
Figure 34:
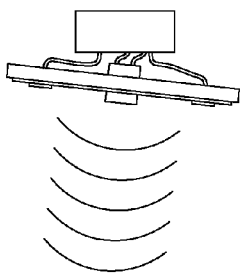
Figure 37:
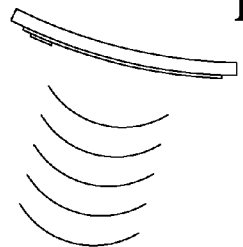

Referring to FIGS. 32-34 certain advantages of vibrator assembly 31 can best be seen. In conventional nebulizers, only one vibrator element is provided, and by design the single vibrator element moves in a unidirectional manner. Vibrator elements that encircle a perforated membrane can only move the perforated membrane and support substrate, along a single axis. This causes aerosolized droplets generated by the perforated membrane to be projected outward in the same direction. Thus, aerosolized droplets are projected in-line, behind a previously ejected aerosolized droplet. Because larger droplets are typically ejected with a lower velocity than corresponding smaller droplets, some of the smaller, faster droplets will collide with larger, slower droplets, combining to form even larger droplets still. Ideally, aerosolized droplets should have a diameter that lies in the range of approximately 1-4.5 microns. In order to reduce the likelihood of aerosol deposition in the mouth, throat, and upper airways, it is critical that the droplets be generated in that size range, and that as many of them as possible remain available in that size range for inhalation. Furthermore, because perforations in a perforated membrane do not always produce a consistent size of aerosol droplets, aerosol particle collisions are inevitable. This is especially true when successive oscillations of a perforated membrane occur along the same axis. In these types of conventional configurations, the smaller droplets have a much greater chance of encountering larger droplets.

However, the embodiment of vibrator assembly 31 and the second alternate embodiment of the vibrator assembly 37 do not project the aerosolized droplets (or fluid jets that eventually break up into the aerosolized droplets) in a unidirectional fashion. As can be seen, vibrator assembly 31 utilizes two vibrator elements 46 on opposite ends of the same face, separated by approximately 180 radial degrees from the midpoint of the diaphragm 42. These two vibrator elements 46 may be pulsed in an alternating manner, so as to generate successive oscillations of the vibrator assembly 31 along non-parallel axes, as depicted schematically in FIGS. 33 & 34. In another set of embodiments, the size of vibrator elements 46 may be varied so that one vibrator element 46 is larger than the other vibrator element 46; the amount of material in a cross-sectional segment of the vibrator elements 46 may be varied, for example, so that one vibrator element 46 is thicker or wider than the other vibrator element 46; or the vibrator elements 46 may be created from different materials, thus creating an imbalance in vibration behavior between the vibrator elements 46. Thus, in various embodiments, by projecting subsequent aerosolized particles along different axes, aerosol particle collisions may be reduced, and the aerosol plume widened. In some further sets of embodiments, the ECU may be able to tune, based on the nebulizer data, how often to alternate oscillation between the two vibrator elements 46, how long to oscillate a vibrator element 46 before alternating to the other vibrator element 46, or what sequence to alternate oscillation between the vibrator elements 46.

Similarly, in the second alternate set of embodiments, the vibrator assembly 37 uses a single vibrator element 46 on one side of the vibrator assembly 37 to project aerosolized particles along multiple axes. In various embodiments, the ECU may oscillate the vibrator element 46 at a high frequency, and by using a support substrate 54 formed from material having a rigidity capable of flexing about its width, the vibrator element 46 may be pulsed to create a sweeping motion of the vibrator assembly 37, causing and angular displacement of the diaphragm 42. Thus, the sweeping motion causes a corresponding sweep of the projection path of the aerosolized droplets, in a non-uniform manner, creating a wider plume with greater separation between the aerosolized droplets projected from adjacent perforations. In one set of embodiments, the support substrate 54 may be comprised of a material having a mechanical rigidity and dimensions that allow for elastic deformation of the support substrate 54 across its width at an oscillation frequency of the vibrator element 46. The wider the plume of the aerosol for a given amount of aerosolized droplets, the further apart the aerosolized droplets are on average. Thus, the number of collisions between aerosolized droplets is reduced. This keeps the aerosolized droplets within a desired MMAD range of approximately 1-4.5 microns, with a low GSD.

In embodiments utilizing a horseshoe-shaped or U-shaped vibrator element 48, a similar sweeping motion may be created, allowing aerosolized droplets to be projected outward along different axes, using: manipulations of oscillation frequency; selection of a support substrate 54 having a material rigidity allowing it to flex; varying the amount of material in a cross-sectional segment, for example, by varying the structural thickness, width or density of the vibrator element 48; utilizing a variable, inhomogeneous material composition to construct the vibrator element 48, or a combination of these techniques.

In various embodiments, the operation of the nebulizer system may be as follows. The patient may verify that there is a power supply connected to the nebulizer body 2, via one of the hand held support 4, the controller 14 or the adapter 18. The strength of the battery on the hand held support 4 may be checked via illumination indicators 9. The cap 30 or the sealing lid 34 may be temporarily removed, and the fluid medicament poured into the fluid chamber 20 of the nebulizer body 2. The medicament may flow downward into a cylindrical fluid chamber 20, atop and over the deflection baffle 26 so as to cover the fluid side 60 of the vibrator assembly 31, 35, 37. The patient may actuate the power button 10 into an "ON" position. The power button 10 may be located on the hand held support 4, the controller 14, mobile device 16 as a soft button, or the adapter 18. The patient may then select an operation mode, via a mode selector button 12. Various operation modes may include, without limitation, a continuous mode, timed mode, intermittent mode, and breathe actuation mode.

In the continuous mode, as the patient inhales, the pressure in the aerosol chamber 22 drops below an ambient pressure. In various embodiments, ambient pressure may be a predetermined threshold value, such as, without limitation, 2-3 cm water pressure below atmospheric pressure, while in other embodiments, the ambient pressure may be determined dynamically based on a measured ambient pressure. The ECU may also monitor a flow trigger, for example, in the range of 0.7-2.0 lpm, within which aerosol generation may be initiated. In some sets of embodiments, the pressure sensor 52 may send a low pressure signal to the ECU to begin aerosol generation while pressure in the aerosol chamber 22 remains below a preset level. The ECU may record input data, as reported by one or more pressure sensors, such as when the low pressure signal is received, the duration of the low pressure signal, and the number of low pressure signals received. In various embodiments, the ECU may simultaneously send a driver signal having a frequency corresponding to a desired oscillation frequency to the vibrator element(s) 46, 48. In various embodiments, the vibrator element(s) 46, 48 may be piezoelectric elements, which, when oscillated, cause the support substrate 54 and the diaphragm 42 coupled to the support substrate 54, to vibrate at the same frequency as the driver signal. Atomization may then be initiated nearly instantaneously with oscillation of the vibration mesh 58. In various embodiments, fluid medicament, on a fluid side 60 of the vibrating means 31, 35, 37, may pass through the perforations in the vibration mesh 58, through which the fluid medicaments may be ejected in the form of aerosolized droplets, or fluid jets that eventually break apart into aerosolized droplets.

While the patient is inhaling, an inhalation valve 38 may open to allow a surge of air to help carry the aerosolized medicament out of aerosol chamber 22, and to the patient's lungs. When the patient stops inhaling, the pressure sensor may stop sending its signal to the ECU, which may stop the vibrator elements 46, 48 from vibrating. Correspondingly, the inhalation valve 38 closes. In various embodiment, if continuous or intermittent mode has been selected, the pressure sensor 52 may generate low pressure signals that may be recorded by the ECU, without initializing oscillation of the vibrator elements 46, 48. If the patient exhales into the nebulizer body 2, the exhalation valve 36 may open its flapper valve 40, venting the excess pressure from the nebulizer body 2, and preventing the diaphragm 42 from being exposed to over pressurization damage. The process may then repeat itself until the patient stops or the medicament is depleted. In one set of embodiments, one or more of the diaphragm 58, pressure sensor 52, fluid chamber 20, or aerosol chamber 22 may further include a medicament level sensor to monitor a supply of remaining medicament in the fluid chamber 20. In various embodiments, the ECU, hand held support 4, the controller 14, or the mobile device 16 may interpret input data from any of the pressure sensor 52, diaphragm 42, airflow sensor, medicament level sensor, or any other available sensor, as appropriate, to collect a nebulizer data set for a given session, time period, or on a continuing basis. Thus, the collected nebulizer data may be transmitted, in various embodiments, by any of the ECU, hand held support 4, wall adapter 8, controller 14, mobile device 16, or mobile device adapter 18. The nebulizer data may be visually displayed on the mobile device 16, or further transmitted to an external computer system, such as a medical provider's computer system. In a further sets of embodiments, the nebulizer data may be analyzed by an internal ECU to adjust at least one of an oscillation frequency, duration, or alternation pattern of vibrator elements 46, 48.

Figure 38:
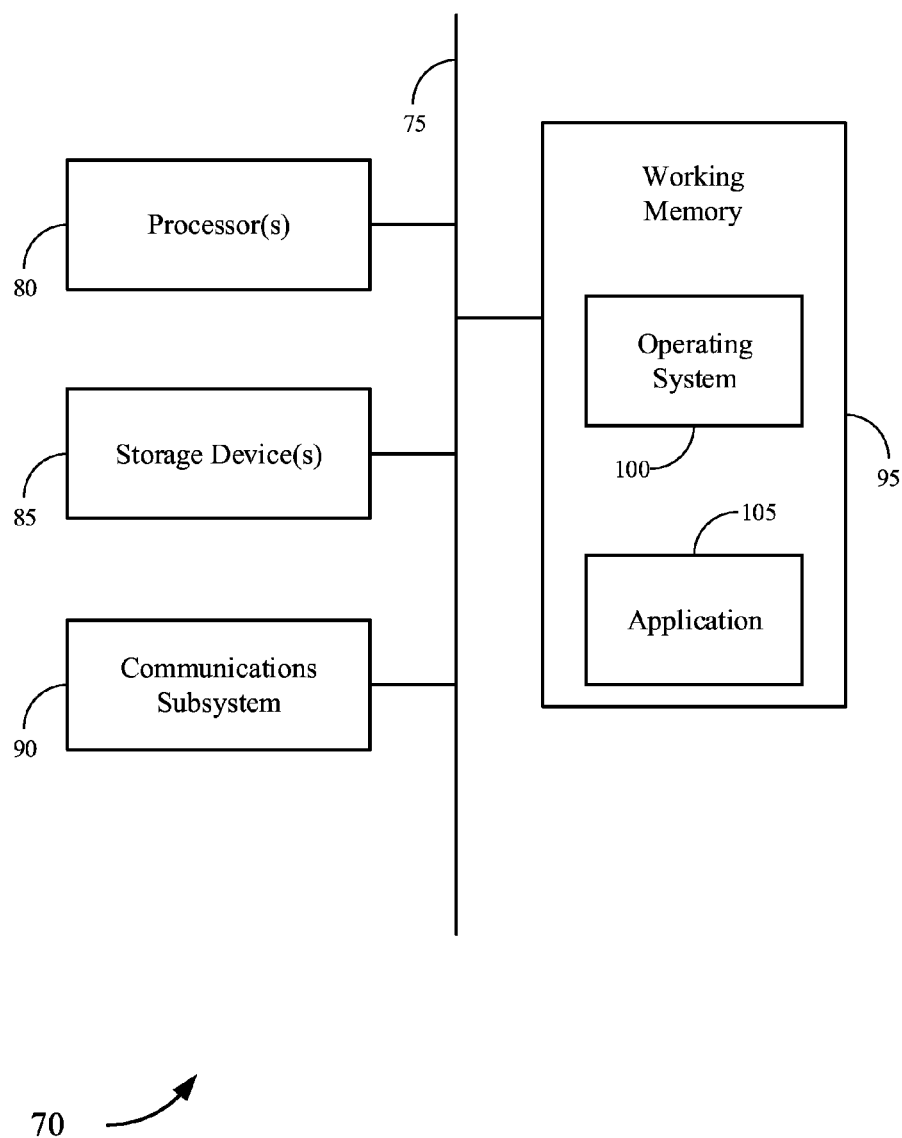
FIG. 38 is a schematic block diagram of computer hardware for an electronic control unit of a nebulizer, in accordance with various embodiments.

FIG. 38 is a schematic block diagram of a computer architecture for a nebulizer system, in accordance with various embodiments. FIG. 38 provides a schematic illustration of a computer system 70 that can perform the methods provided by various other embodiments, as described herein, and/or can perform the functions of the ECU, or nebulizer controller as may be provided in the hand held support 4, wall adapter 8, controller 14, mobile device 16, mobile device adapter 18, or any other computer systems described above. It should be noted that FIG. 38 is meant only to provide a generalized illustration of various components, of which one or more (or none) of each may be utilized as appropriate. FIG. 38, therefore, broadly illustrates how individual system elements may be implemented in a relatively separated or integrated manner.

The computer system 70 includes a plurality of hardware elements that can be electrically coupled via a bus 75 (or may otherwise be in communication, as appropriate). The hardware elements may include one or more processors 80, including, without limitation, one or more general-purpose processors and/or one or more special-purpose processors (such as digital signal processing chips, graphics acceleration processors, and/or the like). In general, embodiments can employ as a processor any device, or combination of devices, that can operate to execute instructions to perform functions as described herein. Merely by way of example, and without limitation, any microprocessor can be used as a processor, including without limitation one or more CISC microprocessors, such as the single core and multicore processors available from Intel Corporation™ and others, such as Intel's X86 platform, including, e.g., the Pentium™, Core™, and Xeon™ lines of processors. Additionally and/or alternatively, reduced instruction set computing RISC microprocessors, such as the IBM Power™ line of processors, processors employing chip designs by ARM Holdings™, and others can be used in many embodiments. In further embodiments, a processor might be a microcontroller, embedded processor, embedded system, SoC, application specific integrated circuit (ASIC), or the like.

As used herein, the term "processor" can mean a single processor or processor core (of any type) or a plurality of processors or processor cores (again, of any type) operating individually or in concert. Merely by way of example, the computer system 70 might include a general-purpose processor having multiple cores, a digital signal processor, and a graphics acceleration processor. In other cases, the computer system might 70 might include a CPU for general purpose tasks and one or more embedded systems or microcontrollers, for example, to run real-time functions. The functionality described herein can be allocated among the various processors or processor cores as needed for specific implementations. Thus, it should be noted that, while various examples of processors 80 have been described herein for illustrative purposes, these examples should not be considered limiting.

The computer system 70 may further include, or be in communication with, one or more storage devices 85. The one or more storage devices 85 can comprise, without limitation, local and/or network accessible storage, or can include, without limitation, a disk drive, a drive array, an optical storage device, a solid-state drive, flash-based storage, or other solid-state storage device. The solid-state storage device can include, but is not limited to, one or more of a random access memory (RAM) or a read-only memory (ROM), which can be programmable, flash-updateable, or the like. Such storage devices may be configured to implement any appropriate data stores, including, without limitation, various file systems, database structures, or the like.

The computer system 70 might also include a communications subsystem 90, which can include, without limitation, a modem, a network card (wireless or wired), a wireless programmable radio, or a wireless communication device. Wireless communication devices may further include, without limitation, a Bluetooth device, an 802.11 device, a WiFi device, a WiMax device, a WWAN device, cellular communication facilities, or the like. The communications subsystem 90 may permit data to be exchanged with one or more sensors, external computer systems, communications networks, mobile devices, other network elements, or combination of the above devices, as described above. According to some embodiments, the network might include a local area network (LAN), including without limitation a fiber network, or an Ethernet network; a wide-area network (WAN); a wireless wide area network (WWAN); a virtual network, such as a virtual private network (VPN); the Internet; an intranet; an extranet; a public switched telephone network (PSTN); an infra-red network; a wireless network, including without limitation a network operating under any of the IEEE 802.11 suite of protocols, the Bluetooth protocol, or any other wireless protocol; or any combination of these or other networks.

In many embodiments, the computer system 70 will further comprise a working memory 95, which can include a RAM or ROM device, as described above. The computer system 70 also may comprise software elements, shown as being currently located within the working memory 95, including an operating system 100, device drivers, executable libraries, and/or other code. The software elements may include one or more application programs 105, which may comprise computer programs provided by various embodiments, and/or may be designed to implement methods and/or configure systems provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 95 described above. In some cases, the storage medium might be incorporated within a computer system, such as the system 70. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the computer system 70 and/or might take the form of source and/or installable code, which, upon compilation and/or installation on the computer system 70 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 70) to perform methods in accordance with various embodiments of the invention. According to a set of embodiments, some or all of the procedures of such methods are performed by the computer system 70 in response to processor 80 executing one or more sequences of one or more instructions (which might be incorporated into the operating system 100 and/or other code, such as an application program 105) contained in the working memory 95. Such instructions may be read into the working memory 95 from another computer readable medium, such as one or more of the storage device(s) 85. Merely by way of example, execution of the sequences of instructions contained in the working memory 95 might cause the processor(s) 80 to perform one or more procedures of the methods described herein.

The terms "machine readable medium" and "computer readable medium," as used herein, refer to any medium that participates in providing data that causes a machine to operation in a specific fashion. In an embodiment implemented using the computer system 70, various computer readable media might be involved in providing instructions/code to processor(s) 80 for execution and/or might be used to store and/or carry such instructions/code (e.g., as signals). In many implementations, a computer readable medium is a non-transitory, physical and/or tangible storage medium. In some embodiments, a computer readable medium may take many forms, including but not limited to, non-volatile media, volatile media, or the like. Non-volatile media includes, for example, optical and/or magnetic disks, such as the storage device(s) 85. Volatile media includes, without limitation, dynamic memory, such as the working memory 95.

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 80 for execution. Merely by way of example, the instructions may initially be carried on a magnetic disk and/or optical disc of a remote computer. A remote computer might load the instructions into its dynamic memory and send the instructions as signals over a transmission medium and/or received and/or executed by the computer system 70. These signals, which might be in the form of electromagnetic signals, acoustic signals, optical signals and/or the like, are all examples of carrier waves on which instructions can be encoded, in accordance with various embodiments of the invention.

The communications subsystem 90 (and/or components thereof) generally will receive the signals, and the bus 75 then might carry the signals (and/or the data, instructions, etc. carried by the signals) to the processor(s) 80, or working memory 95, from which the processor(s) 80 retrieves and executes the instructions. The instructions received by the working memory 95 may optionally be stored on a storage device 85 either before or after execution by the processor(s) 80.

According to a set of embodiments, the computer system 70 may be an ECU of the nebulizer. In other embodiments, may be a nebulizer controller of the hand held support 4, wall adapter 8, controller 14, mobile device 16, or mobile device adapter 18.

Figure 39:
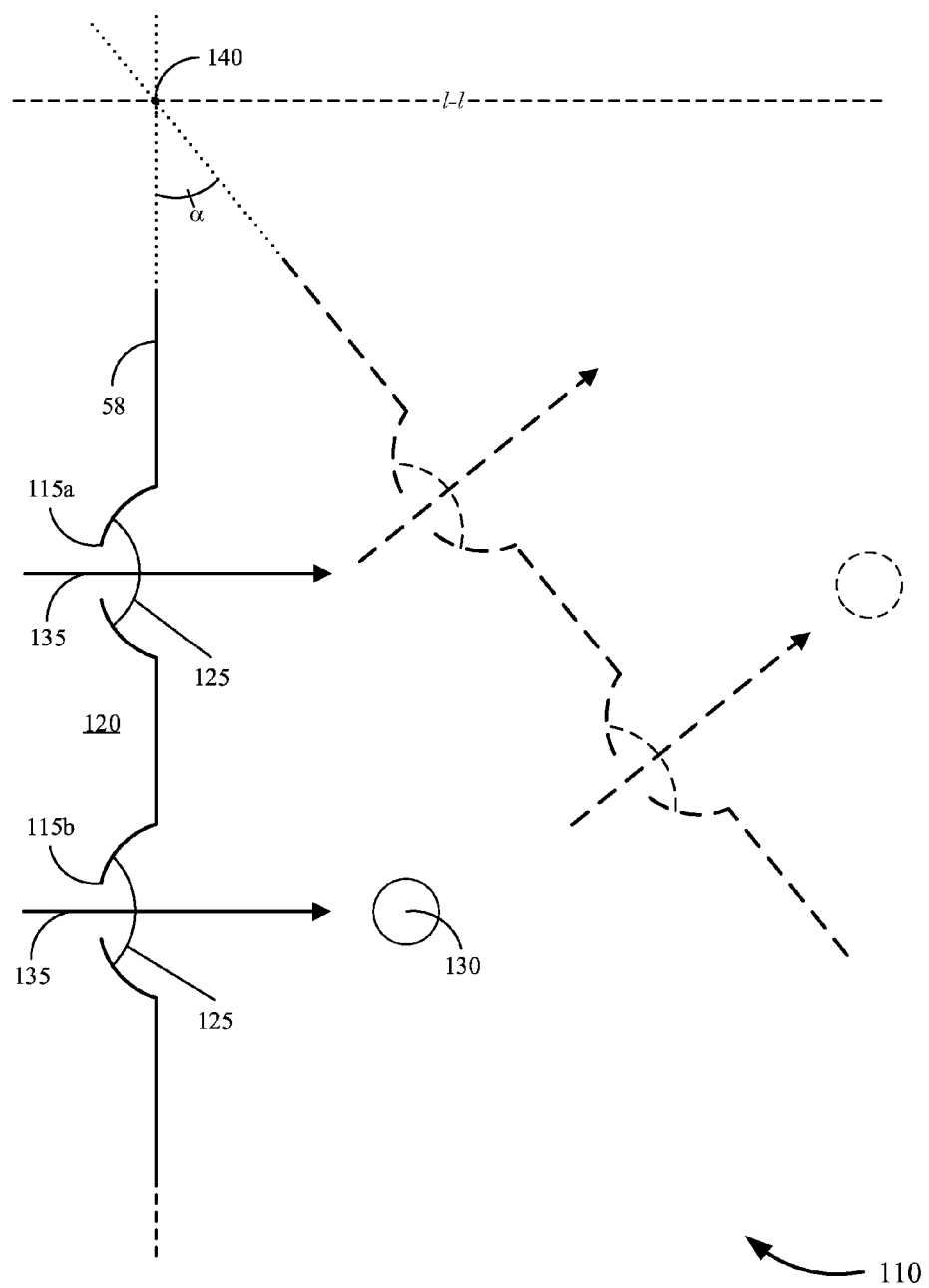
FIG. 39 is a schematic illustration of a diaphragm of a vibrator assembly being swept in contact with fluid medicament, in accordance with various embodiments.

FIG. 39 is a schematic illustration 110 of a partial, cross-sectional side view of a diaphragm 42 being swept. According to various embodiments, diaphragm 42 includes a plurality of perforation 115a, 115b (115 collectively) at an interface 125 between fluid medicament 120 in a fluid chamber, and an aerosol chamber 22. When the diaphragm 42 is vibrated by one or more vibrator elements, an aerosolized droplet 130 is projected through the perforation 115b along a projection path 135. Each perforation 115a, 115b may respectively project an aerosolized droplet 130 along a projection path 135 that is substantially normal to a plane defined by the aerosol side of the perforation.

In various embodiments, the diaphragm 42 may be swept by one or more vibrator elements to cause an angular displacement $\alpha$, about a pivot point 140. In some sets of embodiments, the pivot point 140 may be configured to coincide with a location of an axis l-l of the aerosol chamber 22. The axis l-l of the aerosol chamber 22 may extend longitudinally through the length of the aerosol chamber 22, and be centered through the length of the aerosol chamber 22. For example, in embodiments where the aerosol chamber 22 has a substantially cylindrical structure, the axis l-l of the aerosol chamber 22 may extend through the center of the bases of the cylinder comprising aerosol chamber 22. In various embodiments, the ECU may oscillate the one or more vibrator elements to create the sweeping motion and angular displacement of the diaphragm 42. Thus, the sweeping motion causes a corresponding sweep of the projection path 135 of the aerosolized droplets 130, in a non-uniform manner, creating a wider plume with greater separation between the aerosolized droplets projected from the adjacent perforations 115.

In one set of embodiments, the ECU, through the one or more vibrator elements, may cause a substantially continuous oscillating sweep of the diaphragm 42, and corresponding projection path 135. In other embodiments, the ECU may cause, through the one or more vibrator elements, the diaphragm 42 to switch between a finite number of sweep position steps, operating in each position for a predetermined amount of time. In yet another set of embodiments, the diaphragm 42, and in some embodiments an accompanying support substrate, may be caused to flex, creating a partial angular displacement of one set of perforations 115a, while causing a different partial angular displace of another set of perforations 115b. Accordingly, flexing of the diaphragm 42 may cause part of the diaphragm 42 to be swept in one direction by a certain amount, and another part of the diaphragm 42 to be swept in a second direction by a different amount. In these embodiments, the projection path 135 of perforation 115a may further differ from the projection path 135 of perforation 115b, corresponding to how much the diaphragm 42 flexes in the proximity of perforations 115a and 115b.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture, but instead can be implemented on any suitable hardware, firmware, and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added, and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A nebulizer system comprising:
a body having a fluid chamber and an aerosol chamber;
a vibrator assembly, positioned at an interface between the fluid chamber and the aerosol chamber, the vibrator assembly comprising:
   a diaphragm having a fluid side in fluid communication with the fluid chamber and an aerosol side in communication with the aerosol chamber, the diaphragm defining a plurality of perforations between the fluid side and the aerosol side; and
   one or more vibrator elements operatively associated with the diaphragm to vibrate the diaphragm to project aerosolized medicament into the aerosol chamber from the plurality of perforations;
   wherein each perforation of the plurality of perforations project the aerosolized medicament along a respective projection path substantially normal to a plane defined by the aerosol side of the perforation, the one or more vibrator elements further being configured to angularly displace the aerosol side of the diaphragm to sweep the direction of at least one projection path.

2. The nebulizer system of claim 1, wherein angular displacement of the aerosol side of the diaphragm comprises tilting at least part of the aerosol side of the diaphragm relative to an axis of the aerosol chamber.

3. The nebulizer system of claim 1, wherein the vibrator assembly further comprises:
a support substrate configured to structurally support the diaphragm through a range of motion of the sweep of the at least one projection path; and
wherein the diaphragm further comprises a perforated membrane having the plurality of perforations operatively coupled to the support substrate.

4. The nebulizer system of claim 1, wherein the one or more vibrator elements comprise a pair of vibrator elements.

5. The nebulizer system of claim 1, wherein the one or more vibrator elements comprises a U-shaped vibrator element.

6. The nebulizer system of claim 1, wherein the one or more vibrator elements comprise a single vibrator element.

7. The nebulizer system of claim 1, wherein the one or more vibrator elements has at least one of structurally varying width, thickness, amount of material, or material composition.

8. The nebulizer system of claim 1, further comprising a nebulizer controller in communication with each of the one or more vibrator elements, the nebulizer controller programmed to manage operation of the one or more vibrator elements to sweep the direction of the at least one projection path.

9. The nebulizer system of claim 8, wherein the body comprises at least one communication interface, wherein the at least one communication interface is communicatively coupled to at least one of the one or more vibrator elements and the nebulizer controller, wherein access to at least one of the one or more vibrator elements is provided over the at least one communication interface.

10. The nebulizer system of claim 9, wherein the at least one communication interface comprises a wireless transceiver enabling wireless transmission of nebulizer data to an external computing device.

11. The nebulizer system of claim 9, wherein the at least one communication interface comprises a port for wired connections, wherein the port may simultaneously provide data transmission and act as an electrical power source.

12. The nebulizer system of claim 9, further comprising a pressure transducer within the body, and communicatively coupled to at least one of the nebulizer controller or an at least one communication interface, wherein the pressure transducer transmits a low pressure signal in response to detecting a decrease in local pressure of the aerosol chamber, below an ambient pressure, and exceeding a threshold decrease in pressure, wherein the nebulizer controller actuates the one or more vibrator elements only while the pressure transducer continues to indicate, via the low pressure signal, that the decrease in local pressure in the aerosol chamber exceeds the threshold decrease in pressure.

13. The nebulizer system of claim 12, wherein the nebulizer controller is further programmed to:
collect, as input data from the pressure transducer, at least one of a number of nebulizer uses, duration of each nebulizer use, number of breaths taken for each nebulizer use, and length of each inhalation;
determine, based on the input data, at least one of a time of occurrence of the low pressure signal, a date of occurrence of the low pressure signal, or duration of the low pressure signal; and
wherein the input data, the time of occurrence of the low pressure signal, the date of occurrence of the low pressure signal, and the duration of the low pressure signal forms at least part of compiled nebulizer data.

14. The nebulizer system of claim 13, wherein the nebulizer controller is further programmed to determine an aggregate amount of aerosolized medicament delivered to the patient based, at least in part, on the compiled nebulizer data.

15. The nebulizer system of claim 13, wherein the nebulizer controller is further programmed to:
generate a driver signal, for each of the one or more vibrator elements, having at least a frequency corresponding to a desired oscillation frequency respectively for each of the one or more vibrator elements; and
adjust the driver signal, based on input data received from the pressure transducer.

16. The nebulizer system of claim 8, wherein the nebulizer controller comprises, at least one of, an electronic control unit of the vibrator assembly, hand held support, wall adapter, external controller, mobile device, or mobile device adapter.

17. A nebulizer controller in communication with one or more non-annular vibrator elements, the controller comprising:
at least one processor;
non-transitory computer readable media having encoded thereon computer software comprising a set of instructions executable by the at least one processor to:
   generate a driver signal, for each of the one or more vibrator elements, having at least a frequency corresponding to a desired oscillation frequency respectively for each vibrator element of the one or more vibrator elements;
   vibrate, via the one or more vibrator elements, a vibrator assembly positioned at an interface between a fluid chamber and aerosol chamber of a nebulizer body, the vibrator assembly having a diaphragm with a fluid side in fluid communication with the fluid chamber and an aerosol side in communication with the aerosol chamber, the diaphragm defining a plurality of perforations between the fluid side and the aerosol side;
   project, via the vibrator assembly, aerosolized medicament into the aerosol chamber, wherein each perforation of the plurality of perforations projects the aerosolized medicament along a respective projection path substantially normal to a plane defined by the aerosol side of the perforation; and
   sweep, via the one or more vibrator elements, a direction of at least one projection path of the aerosolized medicament, wherein vibration of the one or more vibrator elements angularly displaces the aerosol side of the diaphragm.

18. The nebulizer controller of claim 17, wherein the set of instructions are further executable to:
retrieve, from a pressure transducer, a measurement of a local pressure in the aerosol chamber;
determine, via the pressure transducer, whether the local pressure has decreased below an ambient pressure;
determine whether a threshold decrease has been exceeded by the local pressure; and
transmit, in response to determining that the threshold decrease has been exceeded, the driver signal to the one or more vibrator elements.

19. The nebulizer controller of claim 18, wherein the set of instructions are further executable to:
collect, as input data, at least one of a number of nebulizer uses, duration of each nebulizer use, number of breaths taken for each nebulizer use, and length of each inhalation; and
determine, based on the input data from the pressure transducer, at least one of a time of occurrence of the low pressure signal, a date of occurrence of the low pressure signal, and signal duration of the low pressure signal, wherein the input data, the time of occurrence of the low pressure signal, the date of occurrence of the low pressure signal, and the duration of the low pressure signal forms at least part of compiled a set of nebulizer data.

20. The nebulizer controller of claim 19, wherein the set of instructions are further executable to determine an aggregate amount of aerosolized medicament delivered to the patient based, at least in part, on the compiled nebulizer data.

21. The nebulizer controller of claim 19, wherein the set of instructions are further executable to:
store, at the nebulizer controller, the compiled nebulizer data; and
transmit the nebulizer data to an external computing device.

22. A method for a nebulizer system comprising:
providing a nebulizer body having a fluid chamber and an aerosol chamber;
providing, at an interface between the fluid chamber and aerosol chamber, a vibrator assembly;
generating, at a nebulizer controller, a driver signal for each of one or more vibrator elements, the driver signal having at least a frequency corresponding to a desired oscillation frequency respectively for each of the one or more vibrator elements;
vibrating, via the one or more vibrator elements, the vibrator assembly, the vibrator assembly having a diaphragm with a fluid side in fluid communication with the fluid chamber and an aerosol side in communication with the aerosol chamber, the diaphragm defining a plurality of perforations between the fluid side and the aerosol side;
projecting, via the vibrator assembly, aerosolized medicament into the aerosol chamber, wherein each perforation of the plurality of perforations project the aerosolized medicament along a respective projection path substantially normal to a plane defined by the aerosol side of the perforation; and
sweeping, via the one or more vibrator elements, a direction of at least one projection path of the aerosolized medicament, wherein vibration of the one or more vibrator elements angularly displaces the aerosol side of the diaphragm.

23. A nebulizer system comprising:
a body having a fluid chamber and an aerosol chamber;
a vibrator assembly, positioned at an interface between the fluid chamber and the aerosol chamber, the vibrator assembly comprising:
a diaphragm having a fluid side in fluid communication with the fluid chamber and an aerosol side in communication with the aerosol chamber, the diaphragm defining a plurality of perforations between the fluid side and the aerosol side;
one or more vibrator elements operatively associated with the diaphragm to vibrate the diaphragm to produce aerosolized medicament projected into the aerosol chamber from the plurality of perforations, wherein each perforation of the plurality of perforations project the aerosolized medicament along a respective projection path relative to a plane defined by the aerosol side of the perforation;
a pressure sensor operatively associated with the diaphragm configured to measure a local pressure of the aerosol chamber; a controller in communication with each of the one or more vibrator elements and the pressure sensor, the controller, in response to receiving a signal from the pressure sensor indicating that the local pressure has decreased below a threshold level, initializing actuation of the one or more vibrator elements; and
wherein at least one of the one or more vibrator elements, the controller or a diaphragm support substrate are configured to displace the aerosol side of the diaphragm to sweep the direction of at least one projection path.

24. The system of claim 23, wherein the pressure sensor is further configured to measure at least one of a number of nebulizer uses, duration of each nebulizer use, number of breaths taken for each nebulizer use, and length of each inhalation.

25. The system of claim 24, further comprising the nebulizer controller being programmed to:
receive input data from the pressure sensor, wherein the input data includes at least one of the number of nebulizer uses, the duration of each nebulizer use, the number of breaths taken for each nebulizer use, and the length of each inhalation; and
determine, based on the input data, at least one of a time of occurrence of each nebulizer use, a date of occurrence of each nebulizer use, or a length of time for each nebulizer use;
wherein the input data, the time of occurrence of each nebulizer use, the date of occurrence of each nebulizer use, and the length of time for each nebulizer use form at least part of compiled nebulizer data.

26. The system of claim 25, wherein the nebulizer controller is further programmed to determine, as part of the compiled nebulizer data, at least one of a diaphragm aerosolized medicament output per unit of time, an amount of time the diaphragm was vibrated, or a volume of a fluid medicament aerosolized by the vibrator assembly.

27. The nebulizer system of claim 26, wherein:
the nebulizer controller is further programmed to determine an aggregate amount of aerosolized medicament delivered to the patient based, at least in part, on the compiled nebulizer data.

28. The nebulizer system of claim 23, wherein the body further comprises at least one communication interface communicatively coupled to each of the one or more vibrator elements and the pressure sensor, wherein access to the at least one vibrator elements and the pressure sensor is provided over the at least one communication interface.

29. The nebulizer system of claim 28, wherein the at least one communication interface comprises a port that simultaneously provides data transmission and electrical power.

* * * * *